ELECTROENCEPHALOGRAPH MONITORING APPARATUS

Original Filed July 13, 1971 6 Sheets-Sheet 1

ELECTROENCEPHALOGRAPH MONITORING APPARATUS

Original Filed July 13, 1971 6 Sheets-Sheet 5

ELECTROENCEPHALOGRAPH MONITORING APPARATUS

Original Filed July 13. 1971 6 Sheets-Sheet 5

ELECTROENCEPHALOGRAPH MONITORING APPARATUS

Original Filed July 13, 1971 6 Sheets-Sheet 6

United States Patent Office

Re. 28,214
Reissued Oct. 29, 1974

28,214
ELECTROENCEPHALOGRAPH MONITORING APPARATUS

Douglas Edward Maynard, Wentworth,
Stoke Poges Lane, England

Original No. 3,699,947, dated Oct. 24, 1972, Ser. No. 162,165, July 13, 1971, which is a continuation-in-part of abandoned application Ser. No. 771,192, Oct. 28, 1968. Application for reissue Apr. 25, 1973, Ser. No. 354,461

*Claims priority, application Great Britain, Oct. 31, 1967, 49,301/67*

Int. Cl. A61b *5/04*

U.S. Cl. 128—2.1 B 16 Claims

Matter enclosed in heavy brackets [ ] appears in the original patent but forms no part of this reissue specification; matter printed in italics indicates the additions made by reissue.

ABSTRACT OF THE DISCLOSURE

Monitoring equipment is provided for monitoring electrical signals in the human brain. Signals from electrodes attached to the scalp are passed to a band-pass filter where certain interference signals, such as those arising from muscle action and rapid psycho-galvanic responses, are removed. The filter also applies a weighting to equalize the effect of random brain activity over the filter band, and to allow rhythmic activity to be more clearly observed. A logarithmic amplifier is connected to the filter output to provide amplitude compression signals received from the brain. The impedance between the electrodes is monitored to give an indication if the electrodes become wholly or partially disconnected.

This application is a continuation-in-part of Ser. No. 771,192, filed Oct. 28, 1968, now abandoned.

The present invention relates to apparatus for monitoring electrical signals in the human brain and to apparatus for monitoring the impedance of electrodes attached to the body and used particularly, but not exclusively, in the signal-monitoring apparatus.

In some circumstances, such as recovery from prolonged cardiac arrest, changes in the electroencephalogram (EEG) over a period of hours to a few days are important. Continuous EEG recording is not practical since it is excessively costly, so EEG sampling by multichannel recorders is used. It has been shown that the sampling techniques are inadequate in assessing a patient's state and can sometimes give misleading results.

The present invention springs from the realization that the EEG shows two main forms of activity: so-called random activity whose amplitude falls with frequency, and rhythmic activity which is partly spread over the same band as the random activity and partly takes the form of sinusoidal signals of widely fluctuating amplitudes, those of greatest amplitude usually occurring in the range 8 to 12 cycles per second (c/s).

According to the present invention there is provided apparatus for monitoring electrical signals in the human brain, comprising a pair of electrodes, adapted to be fixed to the scalp, coupled to a filter of the type hereinafter specified in which the lower predetermined frequency is above 0.3 c/s and the upper predetermined frequency is below 30 c/s, respectively, and in which the frequency versus loss characteristic falls with increase in frequency between the lower and upper predetermined frequencies, so as to in operation substantially equalize the amplitude of filter output signals due to random electrical activity of the brain, means for amplifying signals which pass through the filter, and indicator means for indicating the amplitude of signals from said amplifier means.

In this specification a filter of the type specified has a frequency versus loss characteristic (that is the logarithm of frequency plotted against loss in decibels) in which loss decreases with increase in frequency at a generally constant rate from a low frequency to a high frequency designated at the lower predetermined frequency and the upper predetermined frequency, respectively. As frequency falls below the lower predetermined frequency, or rises above the upper predetermined frequency, loss increases at a rate greater than the said generally constant rate.

The importance of the frequency versus loss characteristic of the filter will now be appreciated; that is all frequency components of the random activity falling within the passband of the filter are equally represented, and the sinusoidal signals are prominent in the output instead of being swamped by the low-frequency random activity.

Preferably the apparatus includes a detector and a recorder and/or meter.

By using the filter the trace provided by the recorder is converted from a form in which little information of a useful character can be obtained to one in which changes in the activity of the brain can readily be observed, especially relatively long term changes occurring in times of for example half an hour. Such changes are difficult or impossible to observe on conventional EEG devices and often give considerable warning, of for example an hour, of cardiac arrest, an instant indication that all is not well during surgical operations, and where resuscitation is being attempted an indication that success will be achieved many hours before any other signs of return to consciousness are seen.

The output from this apparatus being in a simple form, can to a large extent be interpreted by medical and nursing staff who have had experience of the apparatus. A far clearer indication of trends is obtained than from successive EEG recordings, and it is believed that operation could be carried out by relatively unskilled staff.

Since the apparatus is inexpensive, continuous monitoring is practicable and when used in conjunction with occasional EEG samples on a multi-channel recorder gives almost as much relevant information as would be obtained by continuous EEG recording.

The frequency versus loss characteristic of the filter preferably falls at a generally constant rate which provides a loss decrease of between 4 and 12 db over the range 3 to 12 c/s.

Although in some circumstances it may be convenient if the filter has the frequency range mentioned above, the upper predetermined frequency of the filter is preferably variable from 15 c/s to 5 c/s and the lower predetermined frequency is variable from 2 c/s to 12 c/s.

The electrodes are preferably coupled to the filter by way of a low noise amplifier which may be a parametric amplifier, and the output from the filter is amplified by a logarithmic or semi-logarithmic amplifier in order to compress the amplitude of the output signal.

The impedance associated with electrodes attached to the body tends to be subject to changes and, of course, the electrodes may become completely disconnected. This is a weakness of the apparatus, although the parametric amplifier can be designed to give only a 1 percent error in gain when the electrode impedance has risen to about 80 Kilohms. At such impedance however the apparatus becomes more sensitive to interference.

According to another aspect of the present invention therefore there is provided apparatus for monitoring impedance between electrodes comprising a reactive component coupled between a pair of electrodes, each electrode being suitable for attachment to the human body, and the reactive component being coupled with a further impedance across the output of an oscillator, and phase comparison means for comparing the phase of two signals in the apparatus to provide an output signal dependent on the phase relationship of the said signals, the apparatus being such that if, when the electrodes are attached to a human body, the impedance between the body and the electrodes changes, then a change in the said phase relationship is indicated by the output signal of the phase comparison means.

The reactive component is preferably a capacitor and the further impedance a resistor. The electrodes may, of course, be those of the signal-monitoring apparatus, if the oscillator frequency is outside the passband of the filter.

Certain embodiments of the invention will now be described by way of example with reference to the accompanying drawings in which.

Figure 1:
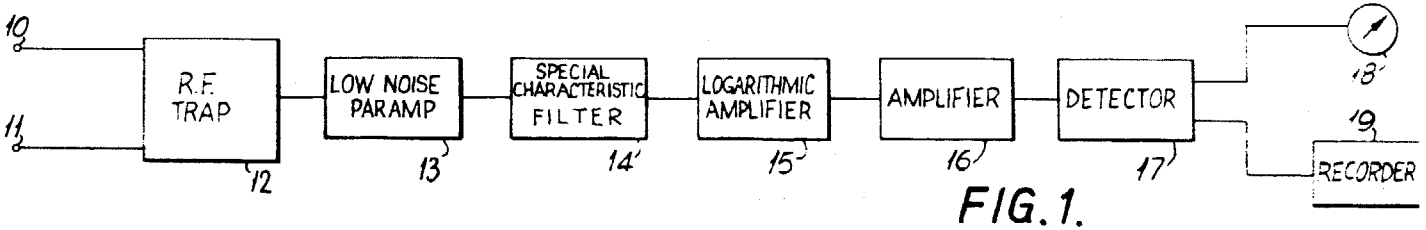
FIG. 1 is a block diagram of apparatus according to one aspect of the invention for monitoring electrical signals in the human brain.
Figure 9:
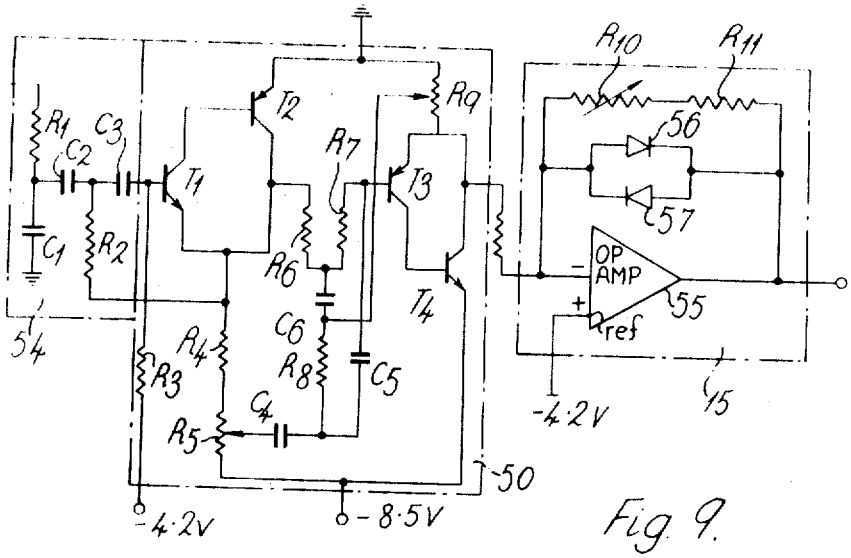
Figure 10:
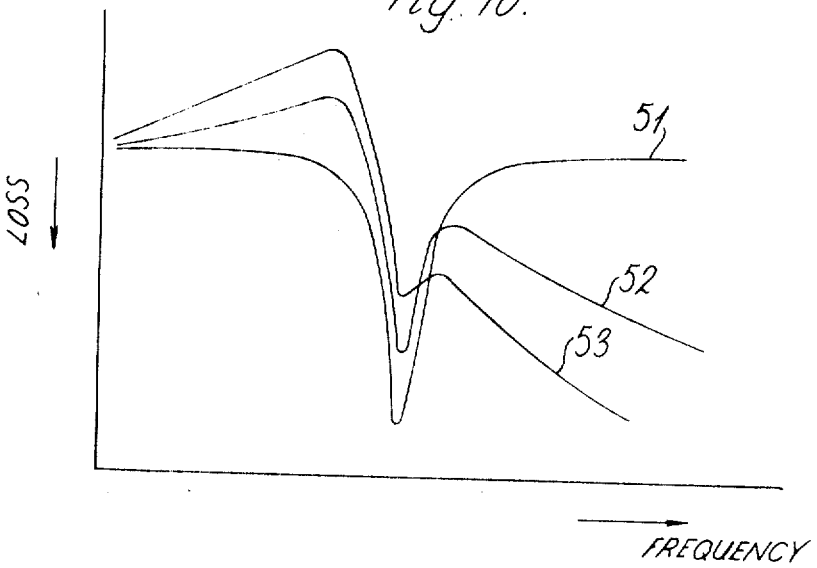

FIG. 9 is a part-circuit part-block diagram of the filter 14 and the amplifier 15 of FIG. 1; and FIG. 10 is a loss versus frequency characteristic used in explaining the setting up of the filter 14.

Figure 6:
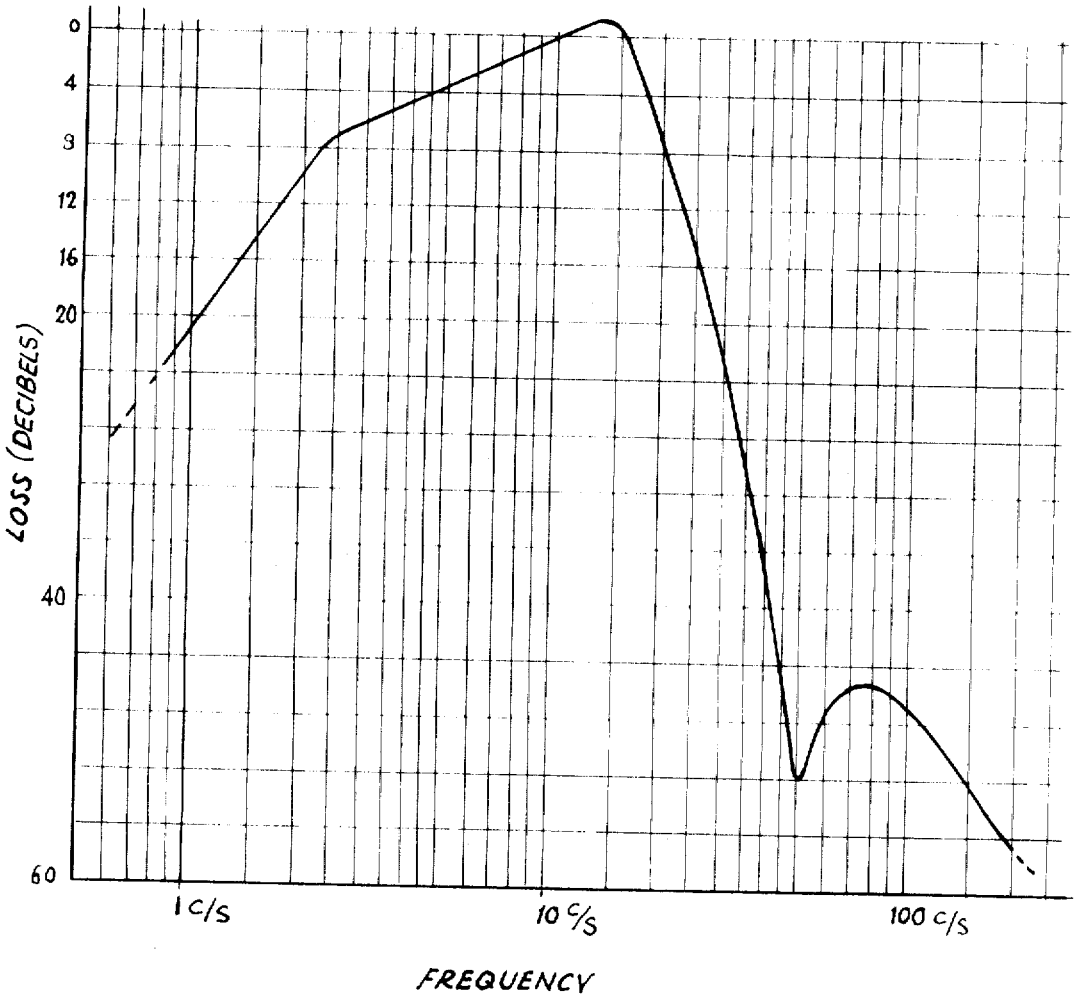
FIG. 6 shows the loss versus frequency characteristic of the filter of FIG. 1.

In FIG. 1 two silver-disc electrodes 10 and 11 are, in use, attached to the scalp to pick up electrical signals in the brain. The electrodes are coupled by way of fully screened cables whose characteristics do not vary with vibration i.e., the cables are non-microphonic to a low pass filter 12 which acts as a radio-frequency trap preventing high frequency interference reaching a low-noise parametric amplifier 13. A special filter 14 which has the weighted loss versus frequency characteristic shown in FIG. 6, is coupled to the output of the amplifier 13. Signals from the filter are amplified first by a logarithmic amplifier 15 which provides amplitude compression, and then by an amplifier 16. A detector 17 provides a signal for a meter 18 and a recorder 19, from the output of the amplifier 16.

The Isleworth Electronics pre-amplifier A101 is suitable as the parametric amplifier 13, especially if specified as having selected low noise input transistors, but many low noise differential amplifiers are suitable such as the Burr Brown instrumentation amplifiers nos. 3161/25 and 3061/25.

The loss versus frequency characteristic of the filter 14 which is one of the most important features of the invention will now be described, and then the construction of filters with this characteristic will be discussed.

As can be seen from FIG. 6, to reduce the effect of interference of originating from muscle action potentials without rejecting significant rhythmic activity of cortical origin, the loss introduced by the filter 14 rises abruptly above a frequency of about 12 c/s. Below a frequency between 2 and 3 c/s loss also increases to reduce the effects of interference originating from a number of sources such as psycho-galvanic responses, sweating, and electrode movement. A high degree of rejection is provided at frequency of the power supply (e.g. 50 c/s in the U.K. as shown in FIG. 6 or 60 c/s in the U.S.A.) to reduce the proportion of amplified antiphase supply frequency components which can occur at the input of the parametric amplifier 13 when connected to a subject to whom other apparatus is attached.

Figure 2:
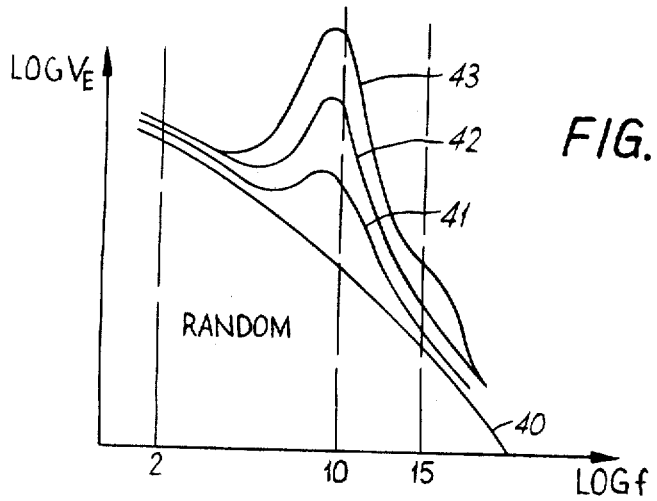
FIG. 2 is a graph showing variation of electrical brain activity with frequency.
Figure 3:
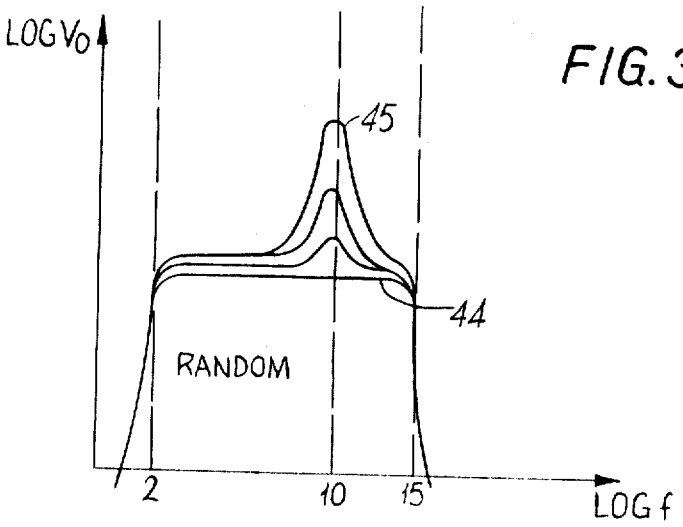
FIG. 3 is a graph showing output signals from the filter 14 of FIG. 1.

Perhaps the most important part of the filter characteristic lies between about 3 c/s and 13 c/s and has been devised following the realization that the electrical activity of the brain can be represented in a simplified form as shown in FIG. 2 for the frequency range indicated where $V_E$ is the voltage between electrodes fixed to the scalp. The random activity mentioned above is represented by the line 40, and the rhythmic activity (that is alpha rhythm) by lines 41, 42 and 43. Since it is random, the random activity conveys no more information at any one frequency than it does at any other. To get a good estimate of its level with a high degree of confidence (a large number of degrees of freedom), it is justifiable to weight the spectrum between about 3 c/s and 13 c/s as shown in FIG. 6 that is to have a decreasing loss with frequency which rises at a rate of 7 db over a frequency range of 4 to 1. This rate of decrease substantially equalizes the amplitude of signals, due to random electrical activity of the brain, at the filter output, and the rate can be obtained from the change in brain activity with frequency of FIG. 2. Fluctuation of high frequency components now have the same degree of effect on the output as do those at low-frequencies, as shown by the line 44 in FIG. 3. The rate at which random activity varies depends to some extent on the person considered and the 7 db rate mentioned above gives a practical filter for general use and represents an average rate. Individual variations are likely to be within −3db to +5 db of the 7 db rate.

It is believed that the major component 43 of the rhythmic activity usually occurs at about 10 cps. If this were to have a small amplitude and the spectrum were not weighted, fluctuation of this component would be swamped by fluctuations of the low frequency random activity. However, by weighting the spectrum, fluctuations of this component are more prominent—as shown at 45 in FIG. 3. When this is added to the random activity, the width of the band written out by the recorder, where the recorder is a slow speed chart recorder, alters (because of the large amplitude fluctuations of the rhythmic components), as does the amplitude distribution within the band.

Therefore the lower edge of the band is expected to indicate the lowest level usually reached by the random activity, assuming that the rhythmic activity is not continuously present, while the upper edge of the band indicates the highest level reached by the rhythmic and/or random activity. The width of the band, its height above the baseline, and the amplitude distribution within the band indicate the type of activity in the signal. The rectified output of random activity would tend to have a Rayleigh amplitude distribution. However, by using a logarithmic amplitude scale, this is converted to a more normal distribution, as well as giving useful amplitude compression. For example, considering the output from the chart recorder, if a component at about 4 c/s with a given amplitude variance were to be compared with a 10 c/s component with the same amplitude and variance, the width of the band drawn by the chart recorder would be nearly the same in the two cases, but they would be displaced by different amounts from the baseline, because of the frequency loss characteristic of the filter. Conversely, if both components formed part of the random activity where the 4 c/s component would usually have a larger amplitude (see line 40 FIG. 2), the displacement for the two components and the width of the band would be approximately the same.

The special characteristic of the filter 14 can be achieved in many known ways, and one such way will now be described in detail.

The major part of the characteristic above about 3 c/s is determined by a filter section 50 (see FIG. 9) of the type known as an unbalanced twin "T" section. Such a filter section may be designed in the way described in Electronic Engineering for Apr. 1967 at page 219 by W. Farrer in an article entitled "A Simple Active Filter with Independent Control Over Pole and Zero Locations," to have at first a balanced characteristic as shown at 51 in FIG. 10 with maximum rejection at a frequency of the power supply. By successively adjusting potentiometers R5 and R9 the section 50 becomes progressively unbalanced and has the characteristics shown at 52 and 53. By measuring the characteristic and adjusting the potentiometers R5 and R9 the required characteristic above 3 c/s of FIG. 6 is obtained. A resistor R1 and a capacitor C1 form a simple R-C low pass filter which provides additional attenuation above 20 c/s.

Below 3 c/s the characteristic depends on a filter section 54 of the type known as a Butterworth high pass filter. Such a filter may be designed in the way described in the Burr Brown Handbook of Operational Amplifier Active Networks at page 82. This handbook is available from the Applications Engineering Section, Burr Brown Research Corporation, International Airport Industrial Park, Tuscon, Arizona.

The characteristic of FIG. 6 can be obtained with the component values given in Table 1 where the designations refer to FIG. 9.

TABLE 1

| Components | Value, KΩ |
|---|---|
| R1 | 33 |
| R2 and R3 | 120 |
| R4 | 1 |
| R5 and R9 | Up to 1 |
| R6 and R7 | 22 |
| R8 | 11 |

| Components | Value or Type |
|---|---|
| C1 | 0.22 μf. |
| C2, C3 and C6 | 0.1 μf. |
| C4 and C5 | 0.5 μf. |
| T1 and T4 | 2N 2484 |
| T2 and T3 | 2 S 304 |

Instead of using a filter of the type shown in FIG. 9, the filter 14 may be designed according to the methods given by S. S. Haykin in his book "Synthesis of R-C Active Filter Networks" published by McGraw Hill, London 1969, see particularly Chapter 4.

Other ways are known in which filters with specific characteristics can be designed and many of these ways are suitable for the design of the filter 14.

The logarithmic amplifier 15 may comprise an operational amplifier 55 with two silicon diodes 56 and 57, for example type 1S44, connected in its feedback path. To provide a smooth gain characteristic for the amplifier 55 at very low voltages where the diodes do not conduct a potentiometer R10 of maximum resistance 50 KΩ and a resistor R11 of resistance 100 KΩ are connected in parallel with the diodes. The amplifier 55 may be one of the commercially obtainable operational amplifiers. The gain of the amplifier 15 applies amplitude compression which is then approximately proportional to the logarithm of the deviation of the input signal from virtual earth at the non-inverting input terminal of the operational amplifier.

Figure 7:
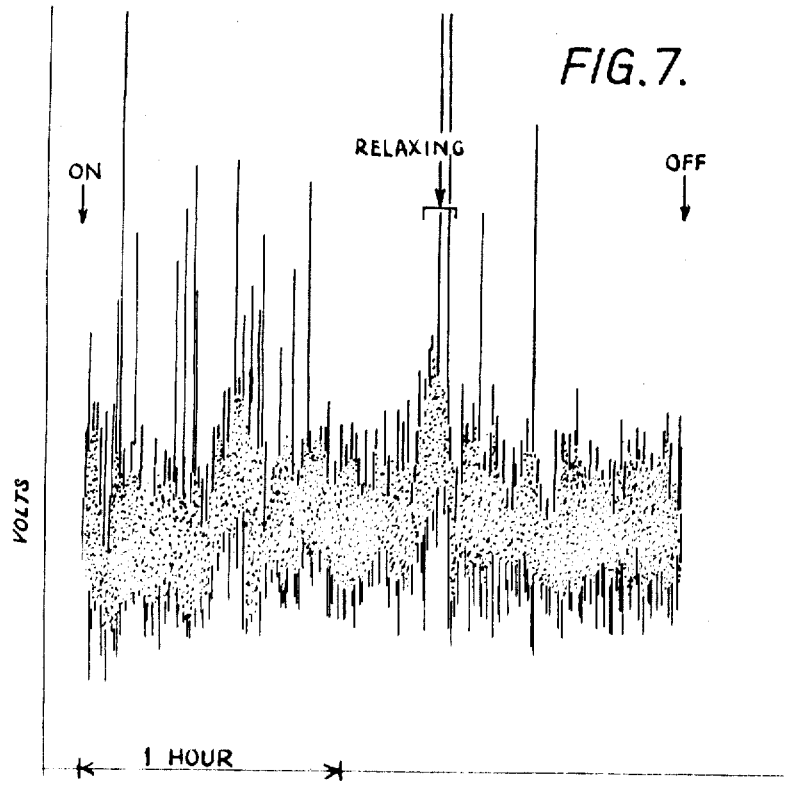
FIGS. 7 and 8 show the output from the recorder of FIG. 1 in different circumstances.
Figure 8:
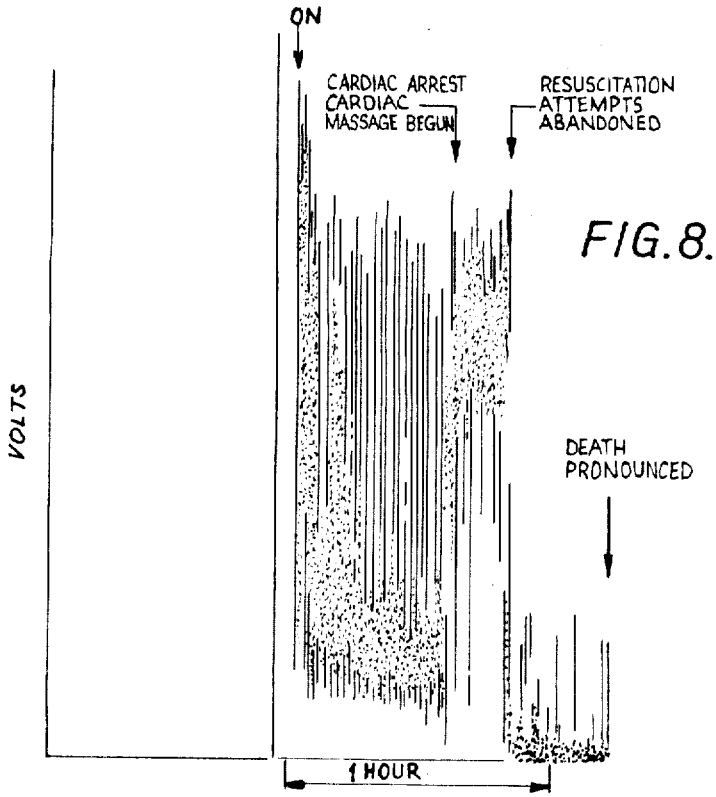

Examples of two outputs obtained from the apparatus of FIG. 1 are given in FIGS. 7 and 8. The recording electrodes 10 and 11 were placed on the scalp of the subjects some two inches posterior to the vertex and some 2½ inches apart symmetrically disposed about the midline. This electrode position was chosen because this is the region in which the largest EEG activity is usually recorded with a minimum of interference from muscle activity, and because it records from both hemispheres simultaneously. A ground electrode, which can be omitted if electrical isolation of the subject is required, was placed on the subject's forehead.

FIG. 7 shows the output from a normal subject performing mathematical calculations and drawing graphs. It can be seen that, over the recorded period, the variation of amplitude remained substantially constant, with occasional larger deflections superimposed. In this case these larger deflections coincided with bursts of alpha rhythms.

By comparison, FIG. 8 shows the output from a patient who had survived a severe cardiac arrest. The electroencephalogram recorded 15 minutes prior to the start of this record had little discernible activity apart from occasional large bursts of sinusoidal waves. It can be seen that the general level of activity steadily declined, to the point where a second cardiac arrest occurred. There followed a brief period of high voltage activity during unsuccessful cardiac massage.

In another case (not illustrated in the figures) a gradual rise in the band of activity from the baseline was the first indication by many hours of the recovery of an unconscious patient suffering from an overdose of barbiturates. Had this indication not been available resuscitation might have seemed hopeless and abandoned.

The usefulness of the write-out can be extended. If the large spikes shown on the declining phase of FIG. 8 had occurred more frequently, the output would have been simply a thick band of activity. To avoid this possibility, an electro-sensitive or heat sensitive write-out system can be used. In this case the write-out can be arranged to have the greatest intensity at those levels most frequently occurring where the pen of the recorder passes several times over the same point on the recording medium giving an amplitude distribution plot of the output by means of varying shades of intensity. This enables different types of EEG activity having different amplitude distribution to be recognized even though they might have the same peak to peak range of variation.

For some work it might prove desirable to have less low frequency activity present in the output. This can be arranged by providing variable sections to the filter which gives the low frequency cut-off point at 2 c/s. By this means the operator can select the appropriate low frequency cut-off point. A similar provision can be made for the higher frequency cut-off point at 15 c/s.

Figure 4:
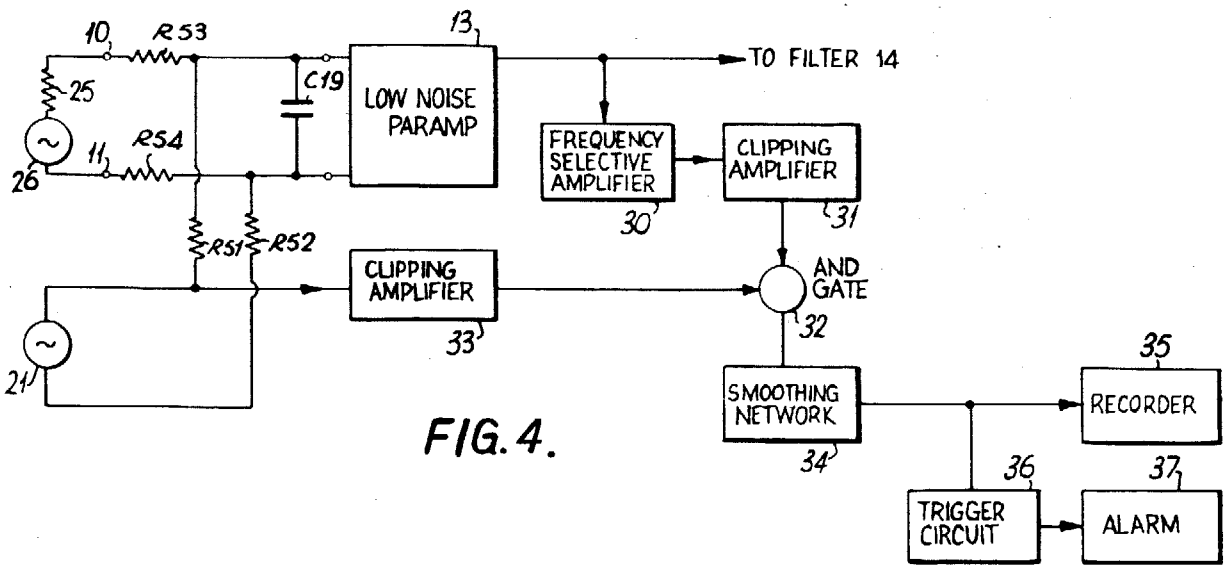
FIG. 4 is a block diagram of apparatus according to another aspect of the invention for monitoring the impedance associated with electrodes attached to the body.

Apparatus for monitoring the impedance of apparatus associated with the electrodes 10 and 11 is shown in FIG. 4.

An oscillator 21 with a frequency which is well above the frequency range of physiological activity of interest, and therefore outside the passband of the filter 14, is applied across the electrodes 10 and 11 through series resistors R51 and R52 which are large compared with the input impedance of the amplifier 13. A small capacitor C19, the impedance of which is negligibly high at the frequency of the physiological activity but not at the frequency of the applied oscillations is connected across the input terminals of the amplifier 13.

The source of signals being monitored is represented by a source impedance 25 and an oscillator 26, the impedance 25 being partly dependent on the conditions of contact between the skin and the disc electrodes.

When the source impedance 25 is small compared with the impedance of the capacitor C19 at the applied frequency, there will be little phase difference between the output signals of the oscillator 21 and the voltage developed across the input terminals of the amplifier 13, since both the capacitor C19 in parallel with the impedance 25 and the complete oscillator load (including the resistors R51 and R52, the capacitor C19 and the impedance 25) are mainly resistive. However, if the impedance 25 increases so that it becomes comparable with or greater than the impedance of the capacitor C19, the impedance 25 and the capacitor C19 taken together become more reactive and a phase lag up to a maximum of 90 degrees is produced at the amplifier input.

To prevent the monitoring voltage applied across the capacitor C19 from disappearing if the electrodes are short circuited, small resistors R53 and R54 of negligible impedance compared to the input impedance of the amplifier 13 are connected in series with the electrode leads.

At the output of the amplifier 13 the signal from the oscillator 21 is separated from the signals from the source 26 by a frequency selective amplifier 30 and formed into a square-wave by a clipping amplifier 31. To compare the phase of the square-wave signal with that of the output signals of the oscillator 21, the square-wave signal is applied to an AND gate 32, together with signals from the oscillator 21 which have been formed into a square-wave by a clipping amplifier 33.

When signals across the capacitor C19 and at the output of the oscillator 21 are in phase, signals arriving at the AND gate 32 by the two paths are out of phase, due to an inversion arranged in one path. Thus the AND gate is not open for in phase oscillator and capacitor signals, but opens, for increasing periods, as the phase difference increases. Consequently the magnitude of the signal from a smoothing network 34 depends on the phase difference and hence on the source impedance 25.

A recorder 35 gives a continuous record of the condition of the electrodes and a trigger circuit 36 operates an alarm 37 when the source impedance rises to an unacceptable level. The trigger circuit 36 may be of any suitable known voltage sensitive type.

A further trigger circuit may be added so that if the impedance falls below a given level, indicating an input short circuit, another alarm circuit may be operated. This alarm circuit may be of such a nature that the chart recorder pen is deflected from the recording area, preventing the recording of inaccurate information.

A further features of the impedance monitor is that it can be arranged to give an indication if the signal from the oscillator 21 is prevented from passing from the amplifier 13 to the amplifiers 30 and 31 by blocking of the amplifier 13 or by circuit failure. This is accompanied by adjusting the bias of clipping amplifier 31 so that, in the absence of an input from amplifier 30 the input to the AND gate 32 switches to the "on" state. Under normal circuit conditions, with a very low source resistance 25, the two inputs to the gate 32 are 180° out of phase and the gate does not open. With a very large source resistance, the two inputs to the gate are 90° out of phase and the gate opens for one quarter of a cycle. With no input to the amplifier 31 the gate is switched solely to the clipping amplifier 33 an input from the amplifier 31 being present permanently, and is open for alternate half cycles.

Therefore it can be seen that, if the output voltage from the smoothing network 34 is zero for a very small source resistance 25 and is V for a very large source resistance then, if the input to the clipping amplifier 31 is removed, the output becomes 2V. Other output configurations can be achieved. For example, by including a 90° phase shift in amplifier 30 the output from the smoothing network 34 can be zero for large source resistance, V for zero source resistance, and 2V for no input to amplifier 31.

Figure 5:
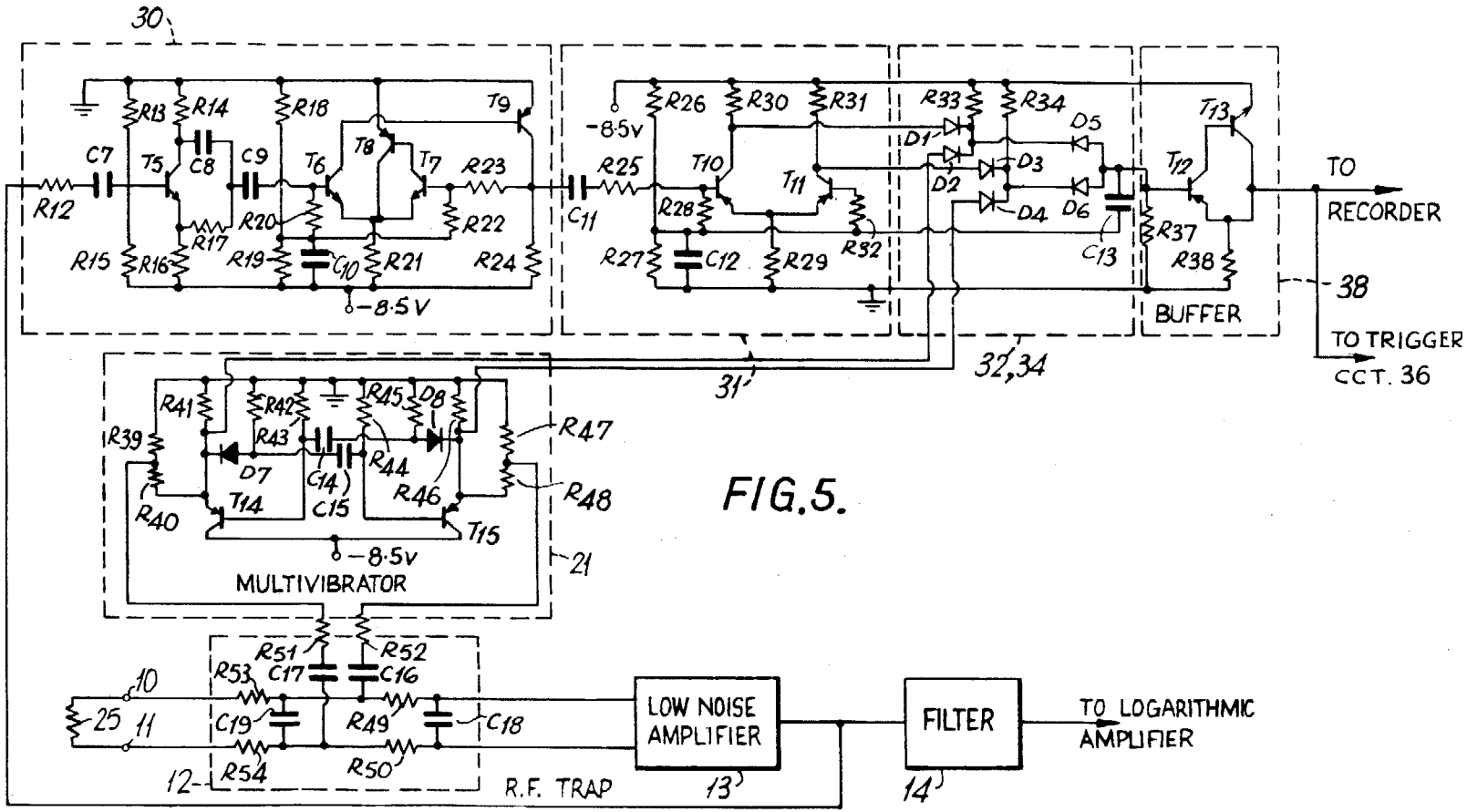
FIG. 5 is a circuit diagram of the apparatus according to FIG. 4 which also shows, partly by means of a block diagram, how the two monitors can be combined.

While suitable circuits for the impedance monitor are well known, a circuit diagram for the above described impedance monitoring equipment including a 90° phase shifter in the amplifier 30 is shown in FIG. 5.

A resistor R12 and a capacitor C7 in the amplifier 30 together with the input impedance of a transistor T5 in parallel with the resistors R13 and R15 form a high pass filter which attenuates frequencies having a physiological origin but which permits the impedance monitoring signal to pass with less attenuation. A capacitor C11 and a resistor R25 with the input impedance of a biasing resistor R28 have the same effect as do a capacitor C9, a resistor R17, the input impedance of a transistor T6 in parallel with a resistor R20. Thus signals of physiological origin are prevented from reaching the clipping amplifier 31.

The resistors R53 and R54 and the capacitor C19 are used as part of the R.F. trap 12. It is convenient to use a multi-vibrator as the oscillator 21, although a square-wave source produces more complicated phase changes across the capacitor C19 than a sine wave. Performance is not much degraded but some phase adjustment may be desirable at the output of the amplifier 13. Since the multivibrator provides a square-wave the clipping amplifier 33 is not required.

Two complementary outputs are taken from the multivibrator to drive two subordinate AND gates made up of diodes D1 and D2, and D3 and D4, respectively. The clipping amplifier 31 also acts as a phase splitter with the collectors of transistors T10 and T11 driven in antiphase. Thus the two subordinate AND gates operate in antiphase and charge is supplied to capacitor 13 twice as frequently as would otherwise occur and the amplitude of the output signal applied to a buffer amplifier 38, provided to drive the recorder and the trigger circuit is doubled. The 90° phase shift in the amplifier 30 is obtained at the junction of the capacitor C8 and the resistor R17 which are driven from antiphase outputs at the collector and emitter of the transistor T5.

Where it is required to indicate loss of the impedance monitoring signal generated by the multivibrator 21, the diodes D3, D4 and D6 are omitted, thus one gate only is provided. Also a resistor (not shown) is added between the base of the transistor T11 and the terminal to which the −8.5V bias is applied. This resistor is individually selected to provide a suitable bias for the AND gate when the monitoring signal is absent. The loss of the input signal then causes the gate to be open for one half of each cycle, zero impedance at the electrodes 10 and 11 opens the gate for a quarter of each cycle and with high impedance the gate is closed during the whole cycle. With such an arrangement the alarm circuit which detects a short circuit input may also be used to detect loss of the monitoring signal.

The circuit of FIG. 5 may be constructed using the components given in TABLE II, where the designations used are those shown in FIG. 5.

TABLE II

| Components | | Value |
|---|---|---|
| R 14, R16, R38 | KΩ | 1 |
| R18, R19, R28 | KΩ | 10 |
| R32, R42, R45 | KΩ | 10 |
| R20, R22, R33, R34 | KΩ | 22 |
| R39, R47 | KΩ | 22 |
| R12, R15 | KΩ | 47 |
| R21, R24, R25 | KΩ | 2.2 |
| R30, R31 | KΩ | 2.7 |
| R53, R54 | KΩ | 2.2 |
| R41, R46, R49, R50 | KΩ | 4.7 |
| R13 | KΩ | 120 |
| R17 | KΩ | 1.5 |
| R23 | MΩ | 1 |
| R26 | KΩ | 6.8 |
| R27 | KΩ | 3.3 |
| R29 | Ω | 680 |
| R37 | KΩ | 330 |
| R40, R48 | KΩ | 56 |
| R43, R44 | KΩ | 82 |
| R51, R52 | MΩ | 70 |

| Components | Value or Type |
|---|---|
| C8, C11, C13 | $0.1_6\mu$f. |
| C7, C14, C15 | 0.01 $\mu$f. |
| C9 | 0.047 $\mu$f. |
| C12, C10 | 1 $\mu$f. |
| C16, C17 | 0.005 $\mu$f. |
| C19 | 0.001 $\mu$f. |
| C18 | 0.002 $\mu$f. |
| T5, T6, T7, T13 | 2 N 3707 |
| T10, T11, T9, T8 | 2 N 3703 |
| T12 | 2 S 304 |
| T14, T15 | 2 N 1304 |
| D1, D2, D3 | 0 A 91 |
| D4, D5, D6 | 0 A 91 |
| D7, D8 | 0 A 91 |

The arrangement of FIGS. 4 and 5 is inherently insentive to changes of gain of the amplifier 13 and since the monitoring voltages are alternating the electrodes are not polarized.

The impedance monitoring apparatus has been specifically described for use with the signal-monitoring apparatus but it could of course be used wherever the impedance associated with electrodes is important.

It is expected that in addition to monitoring of EEG following cardiac arrests the signal-monitoring apparatus will find a useful application in monitoring EEG under long term anaesthesia, with particular emphasis on open heart surgery where the maintenance of a sufficient blood supply to the brain is of critical importance. Apart from warning of imminent cortical extinction, the clear representative of trends should prove to be more convenient than retrospective visual comparisons of conventionally recorded EEG.

A further intended application of the apparatus for monitoring EEG is in studying the effect of drugs and the monitoring of long term sleep changes under various conditions.

I claim:

1. Apparatus for monitoring electric signals in the human brain, comprising:

a pair of electrodes adapted to be fixed to the scalp, filter means coupled to said electrodes, having a frequency versus loss characteristic in which loss decreases with increasing frequency so as to, in operation, substantially equalize the ampliture of the filter output signals due to random electrical activity of the brain, the said decrease in loss with increase in frequency being from a low frequency designated the lower predetermined frequency, to a high frequency designated the upper predetermined frequency, the upper and lower predetermined frequencies being below 30 c/s and above 0.3 c/s, respectively, and loss below the lower predetermined frequency, and above the upper predetermined frequency, being greater than the loss at the lower and upper predetermined frequencies, respectively, amplifying means for amplifying signals which pass through said filter means, and indicator means for indicating the magnitude of signals from said amplifying means.

2. Apparatus according to claim 1, wherein the said filter means has a characteristic, plotted as the logarithm of frequency against loss in decibels, such that said decrease in loss with increase in frequency is at a generally constant rate providing a loss decrease of between 4 and 12 decibels over the range 3 to 12 c/s.

3. Apparatus according to claim 1, wherein said lower predetermined frequency of said filter means is substantially 2 c/s.

4. Apparatus according to claim 1, wherein said lower predetermined frequency of said filter means can be varied from 2 to 12 c/s.

5. Apparatus according to claim 1, wherein said upper predetermined frequency of said filter means is substantially 15 c/s.

6. Apparatus according to claim 1, wherein said upper predetermined frequency of said filter means can be varied from 8 to 20 c/s.

7. Apparatus according to claim 1, comprising low-noise amplifier means coupled between said electrodes and said filter means.

8. Apparatus according to claim 1, wherein said amplifying means includes a logarithmic amplifier.

9. Apparatus according to claim 1, wherein said indicating means includes a detector circuit coupled to said amplifying means and a recorder coupled to said detector means having a pen to mark a recording medium, said recorder being adapted to provide a visible record whose intensity at a point depends on the number of times said pen traverses said point.

10. Apparatus according to claim 1, including monitoring means for monitoring the impedance between said electrodes, comprising reactive means coupled between said electrodes, oscillator means coupled across said reactive means and a further impedance, phase-comparison means for determining the phase relationship of two signals in the monitoring means to provide an output signal, dependent on the phase relationship of the said signals, giving an indication of change in impedance between said electrodes, and indicating means, for indicating said change of phase relationship, coupled to the output of said phase comparison means.

11. Apparatus according to claim 10 wherein said reactive means is a capacitor and the further impedance is a resistor.

12. Apparatus according to claim 11 wherein the capacitor is coupled in series with the resistor across the output of the oscillator and the phase comparision means compares the oscillator output voltage with the voltage across the capacitor.

13. Apparatus according to claim 12 wherein said phase comparison means includes first and second means for forming square-waves from said signals from said oscillator and across said reactive means, respectively, and AND gate means adopted to receive said square-wave signal as inputs, the time during which said AND gate means is open providing said indication of said phase relationship.

14. Apparatus according to claim 13, wherein said AND gate is constructed to become permanently in one state if there is no path for signals from said oscillator by way of said reactive means.

15. Apparatus according to claim 10, wherein the frequency of said oscillator is above the upper predetermined frequency of said filter means, said oscillator is coupled to said electrodes between said electrodes and said filter;

said reactive means is coupled to the input of said filter, and frequency-selective means is provided which is adapted to reject all frequencies present at the input to said filter except that of said oscillator, the input of said frequency selective means being coupled in parallel with the input of said filter, and the output of said frequency selective means is coupled to said phase comparison means.

16. Apparatus for monitoring electrical signals in the human brain, comprising:

a pair of electrodes adapted to be fixed to the scalp, filter means coupled to said electrodes, having a frequency versus loss characteristic in which loss decreases with increasing frequency at a generally constant rate providing a loss decrease of between 4 and 12 decibels over the range 3 to 12 c/s, and loss increases with decrease in frequency below, and with increase in frequency above, the said range at a greater rate than the said rate, amplifying means for amplifying signals which pass through said filter means, and indicator means for indicating the magnitude of signals from said amplifying means.

References Cited

The following references, cited by the Examiner, are of record in the patented file of this patent or the original patent.

UNITED STATES PATENTS

| | | | |
|---|---|---|---|
| 2,490,033 | 10/1946 | Garceau | 128—2.1 |
| 2,657,683 | 11/1953 | Koller | 128—2.1 |

| | | | |
|---|---|---|---|
| 3,123,768 | 3/1964 | Burch et al. | 128—2.1 X |
| 3,185,925 | 5/1965 | Grass | 128—2.1 X |
| 3,195,533 | 7/1965 | Fischer | 128—2.1 |
| 3,212,496 | 10/1965 | Preston | 128—2.1 X |
| 3,347,223 | 10/1967 | Pacela | 128—2.1 |
| 3,452,743 | 7/1967 | Rieke | 128—2.1 |

KYLE L. HOWELL, Primary Examiner

U.S. Cl. X.R.

128—2.1 Z